Figure 1:
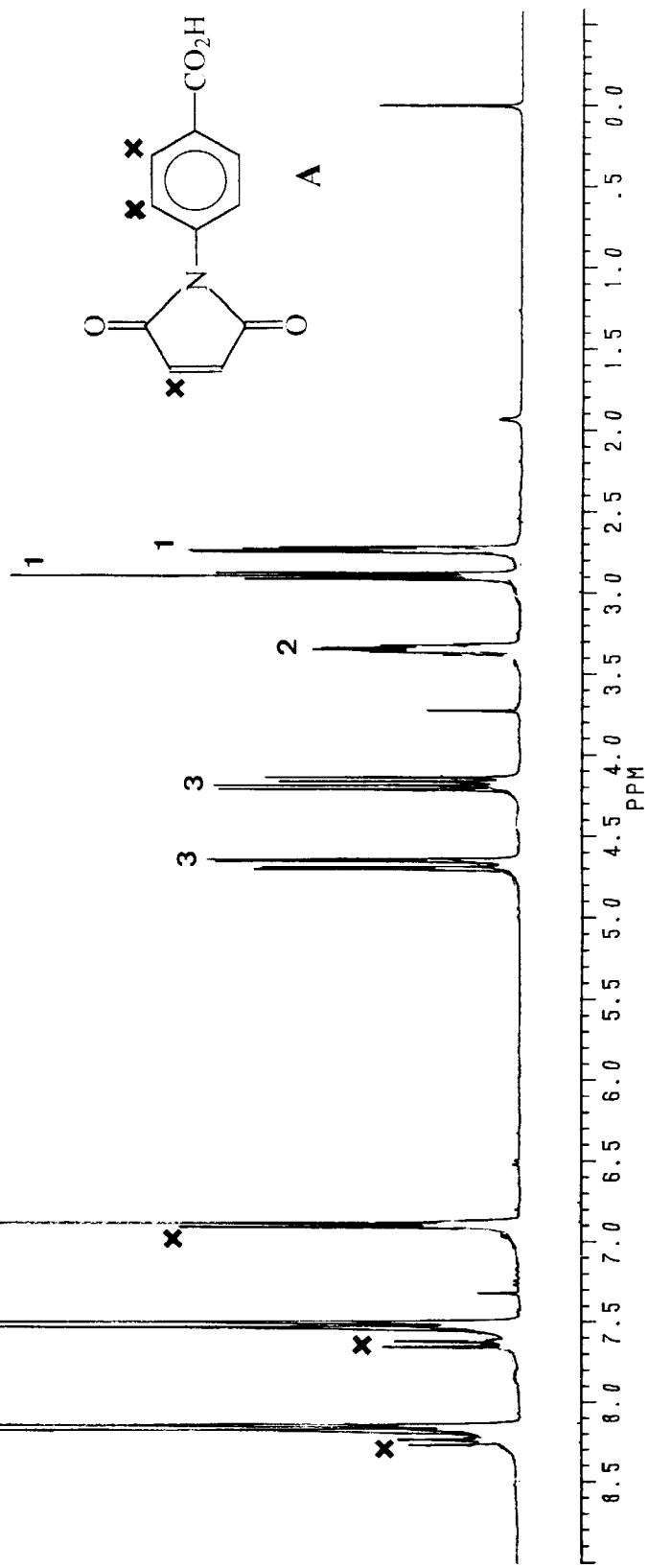

United States Patent

Garapon et al.

[11] Patent Number: 5,981,763
[45] Date of Patent: Nov. 9, 1999

[54] ESTER OF MALEIMIBENZOIC ACID

[75] Inventors: Jacques Garapon; Jacques Vallet, both of Lyons, France

[73] Assignee: Institut Francais du Pëtrole, France

[21] Appl. No.: 08/988,683

[22] Filed: Dec. 11, 1997

[30] Foreign Application Priority Data

Dec. 12, 1996 [FR] France .................................. 96 15472

[51] Int. Cl.⁶ ............................................... C07D 405/10
[52] U.S. Cl. .......................... 548/517; 549/512; 526/352
[58] Field of Search .............................. 548/517; 549/512

[56] References Cited

U.S. PATENT DOCUMENTS 4,158,730  6/1979  Baumann et al. ....................... 528/273

FOREIGN PATENT DOCUMENTS 26 26 769  1/1977  Germany .

OTHER PUBLICATIONS

Serra, et al., New Glycidyl Ester Compounds Containing a Preformed Imide Ring–I, Tetrahedron 41(4), pp. 763–768, Dec. 1983.

Chen et al., Annu. Tech. Conf. Soc. Plast. Eng. (52nd) 2002, Dec. 1994.

*Primary Examiner*—Robert W. Ramsuer
*Assistant Examiner*—Dominic Keating
*Attorney, Agent, or Firm*—Millen, White, Zelano, & Branigan, P.C.

[57] ABSTRACT

Bifunctional compounds are characterized in that they have the following general formula:

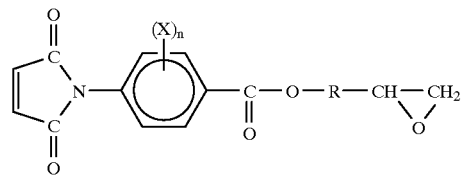

where n is zero or a whole number in the range 1 to 4, limits included, X is a substituent where the X groups are identical or different when n is a number from 2 to 4, and R is a divalent group.

Use of these compounds as functionalising agents for a polyolefin by grafting the compound onto the paraffinic chain, or as compatibilising agents for incompatible polymers.

22 Claims, 2 Drawing Sheets

ESTER OF MALEIMIBENZOIC ACID

The present invention concerns novel bifunctional chemical compounds, their preparation and uses thereof.

During our research into alloys of polymers comprising at least one polyolefin and at least one incompatible polymer, we became interested in polyfunctional compounds containing a function which could readily be grafted onto a paraffinic chain by a radical pathway, and containing a function which could form a bond by an ionic pathway with polymers such as polybutylene-terephthalates or polyamides.

Thus we synthesised compounds containing a double maleimide bond which can form a bond with a paraffinic chain, by a radical pathway, in the presence or absence of a radical initiator, and containing an epoxy group which can react with functional groups, for example the terminal groups of certain polymers.

The compounds of the present invention have formula B given below where n is zero or a whole number from 1 to 4, limits included; X is any substituent, for example a hydrocarbon residue or a halogen atom. When n is a number in the range 2 to 4, groups X can be identical or different. R is a divalent group normally selected from substituted or unsubstituted hydrocarbon residues.

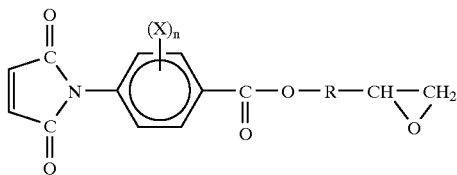

FORMULA B

In the simplest case, n equals zero and the esters formed are those of maleimidobenzoic acid and R is a methylene residue.

These esters of 4-maleimidobenzoic acid, which is substituted or unsubstituted on the benzene ring, with formula A given below, were synthesised to take advantage of the ability of the maleimide function to graft onto a paraffin without a peroxide initiator. Such radical pathway grafting onto a polyolefin is generally carried out with glycidyl methacrylate or other unsaturated derivatives as described, for example, in the article by C. M. CHEN et al., published in Annu. Tech. Conf. Soc. Plast. Eng ($52^{nd}$) 2002, 1994. The role of the epoxy function is to react with acid functions, for example, at the end of a polymer chain to produce ester groups. Thus glycidyl p-maleimidobenzoate with formula B above is capable of reacting simultaneously with the two components of a polyethylene-polybutylene terephthalate alloy (chain ends) during extrusion.

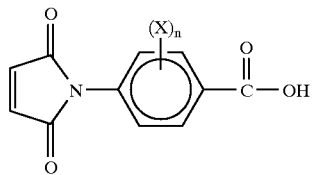

FORMULA A

The compounds of the present invention with formula B above can be obtained by reacting the chloride of maleimldobenzoic acid, which is substituted or unsubstituted on the benzene ring, with an epoxyalcohol, for example glycidol, in a solvent in the presence of a relatively strong base. Tertiary amines are generally used as the base, for example trialkoylamines, in particular triethylamine.

The chloride of the maleimidobenzoic acid which is substituted or unsubstituted on the benzene ring with formula F below is a compound which can be readily obtained, for example by reacting thionyl chloride with the corresponding maleimidobenzoic acid, in the presence of a base. In particular, the chloride of unsubstituted maleimidobenzoic acid (compound with formula F where n equals zero) is described in the literature, for example by B. S. RAO in J. of Polym. Sci. (C) vol. 26, pages 3 to 10, 1988.

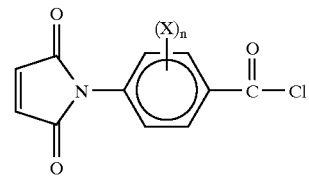

FORMULA F

The compounds with formula B of the present invention can be used as polyolefin functionalising agents, in particular for polyethylenes, by radical pathway grafting of these compounds onto the paraffinic chain of the polyolefin. Grafting can be carried out in the presence of a radical initiator or in the absence of a radical initiator. Generally, it is preferable not to use a radical initiator, in order to avoid any risk of cleavage and cross-liking of the polyolefin. These compounds can also be used as compatibilising agents for incompatible polymers, which means that polymer alloys in particular can be formed. The compounds of the present invention can be used to form alloys of polyolefins with polybutylene-terephthalates or polyamides.

The following example illustrates the invention without limiting its scope.

EXAMPLE 71 g (0.33 M) of maleimidobenzoic acid with formula A where n equals zero, 750 ml of toluene and 0.7 g of pyridine were mixed and 80 ml (1.08 M) of thionyl chloride was rapidly poured in. It was heated to 70° C. and stirred for two hours thirty minutes. After cooling, the solvent and excess reactant were eliminated under vacuum. The chloride of the acid rapidly crystallised. The melting point of the solid obtained was 152.5° C. The melting point of this substance given in the article by F. J. LIU et al., published in the J. of Polym. Sci. (A) vol. 30, pages 157 to 162, 1992, was 153° C. The infrared spectrum of the product in a KBr disk showed the characteristic bands of the imide function and the acid chloride function: wide band at 1780 $cm^{-1}$ and 1720 $cm^{-1}$ (CO imide and acid chloride); 1390 (imide); 1370, 1205, 1180, 1140 and 880 $cm^{-1}$ (acid chloride).

35 g (0.34 M) of triethylamine and 25.5 g (0.34 M) of glycidol were dissolved in 600 ml of 1,2-dichloroethane and this solution was cooled to about +7° C. in a cold bath at −10° C. 77 g (0.33 M) of the chloride of the acid obtained as described above (with formula F where n equals zero) was added over about 30 minutes while controlling the temperature: minimum 7° C., maximum 12° C. After addition, the mixture was stirred at ambient temperature (about 22° C.) for 2 hours. The suspension was directly chromatographed on a fritted glass filtering crucible (diameter 19 cm, height 45 mm) filled with 600 g of silica gel, by eluting with 1,2-dichloroethane (3.5 liters). After evaporating off the solvent, 71.5 g of a beige solid was isolated which melted at 90° C. (80% yield). The ester with formula B, in which n equals zero and R is a methylene group, was recrystallised from methanol. The melting point of the recrystallised solid was 93° C. The nuclear magnetic resonance spectrum showed the presence of maleimidobenzoic acid (quadruplet of aromatic protons at 8.05 and 7.5 ppm in deuterated DMSO). This acid with formula A where n equals zero originated either from hydrolysis during purification by silica gel chromatography (acid) or from imperfect separation during the chromatographic process. The infrared spectrum of the product in a KBr disk showed the characteristic bands of the ester function and of the imide function at 1780 and 1720 cm$^{-1}$ (CO ester and imide); 1380 cm$^{-1}$ (imide); 1270 cm$^{-1}$ (ester).

Figure 2:
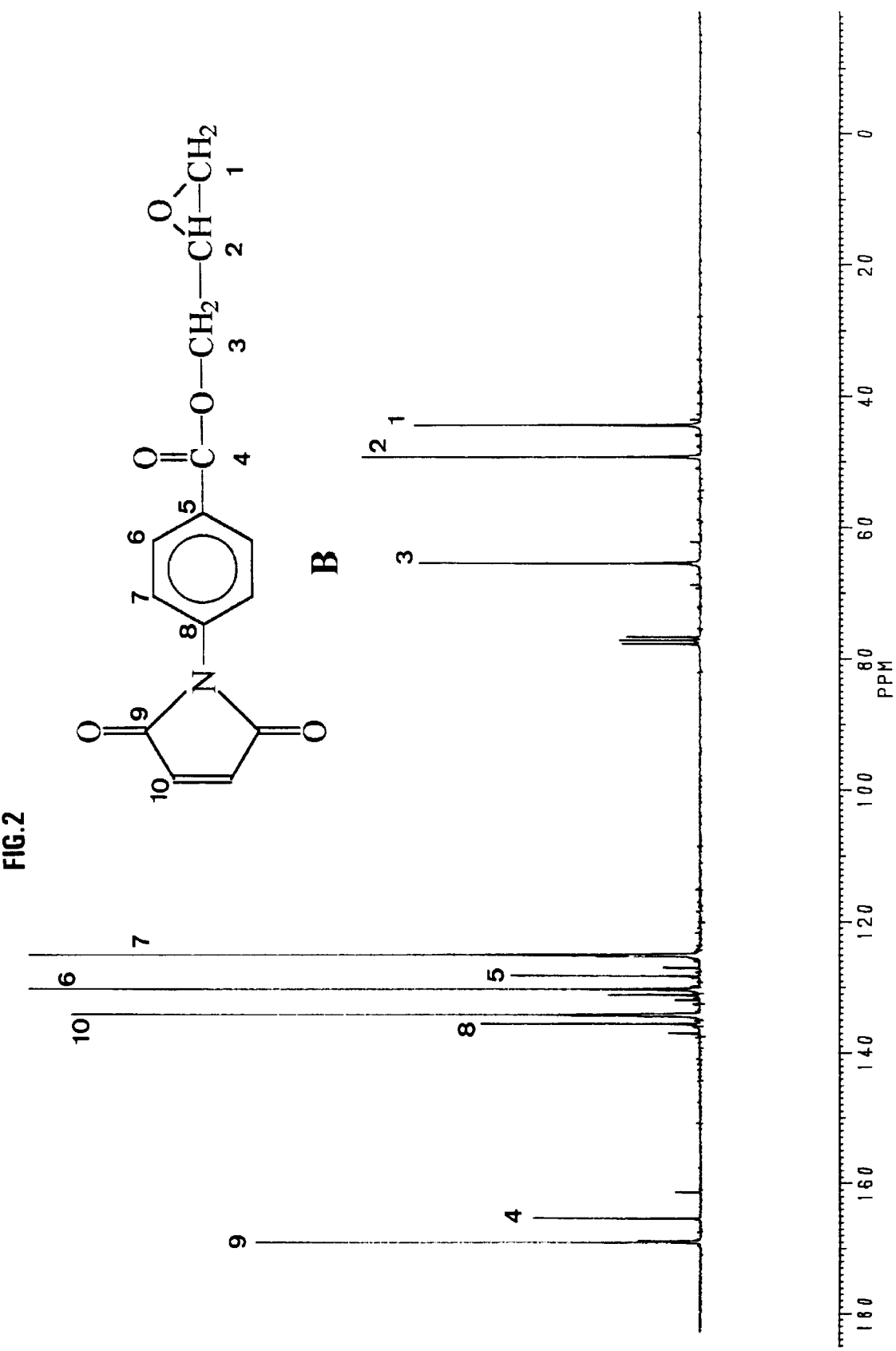

The proton and carbon NMR spectra obtained are shown in FIGS. 1 and 2.

For the addition of a compound of Formula B to a polyolefin, especially polyethylene, any conventional procedure can be used. For example, a procedure can be used which is analogous to examples 1–4 of the concurrently filed application entitled, "Polymer Containing A Succinimide Ring Substituted on the Nitrogen Atom By A Reactive Group" by Camberlain, Gonzalez and Hauviller, Attorney Docket No. PET 1610, priority based on French application 96/15471 filed Dec. 12, 1996. In the examples, 4-maleimidobenzoic acid is grafted onto polyethylene.

Terephthalate and polyamide moieties can then be joined through the epoxy group of Formula B in a conventional manner. The order of steps can be reversed or can be simultaneous. The resultant "alloys" can be used for conventional purposes, for example in the same manner as the composition of U.S. Pat. No. 5,324,779, e.g., for making shaped articles—such as those formed by extrusion, extrusion blow molding or injection molding, e.g., sections, tubes, containers, sheets, films, etc.

The preceding examples can be repeated with similar success by substituting the generically or specifically described reactants and/or operating conditions of this invention for those used in the preceding examples.

The entire disclosure of all applications, patents and publications, cited above, and of corresponding French application 96/15.472, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

We claim:

1. A bifunctional compound for linking two incompatible polymers, wherein the compound has the following formula:

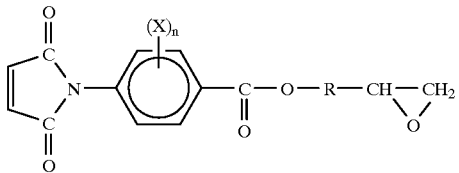

where n is zero or a whole number in the range 1 to 4, limits included, X is a substituted or unsubstituted hydrocarbon group or a halogen atom, where the X groups are identical or different when n is a number from 2 to 4, and R is a hydrocarbon group.

2. A compound according to claim 1, in which R is a substituted hydrocarbon group.

3. A compound according to claim 1, in which R is an unsubstituted hydrocarbon group.

4. A compound according to claim 1, in which R is a methylene group.

5. A compound according to claim 1, in which n equals zero.

6. A process for the preparation of a compound according to claim 1, in which a chloride of an acid with the following formula:

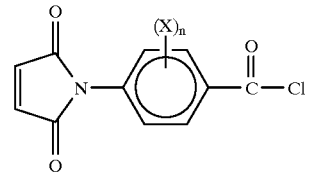

where X and n have the meanings given in claim 1, is reacted with an epoxyalcohol in a solvent in the presence of a relatively strong base.

7. A preparation process according to claim 6, in which the relatively strong base is a tertiary amine.

8. A preparation process according to claim 6, in which the relatively strong base is triethylamine.

9. A method of grafting a compound of claim 1 onto a paraffinic claim of a polyolefin.

10. A method of compatibilizing two incompatible polymers comprising linking at least two incompatible polymers by reacting a compound according to claim 1 with the polymers.

11. A method of use according to claim 10, wherein at least one of the incompatible polymers is a polyolefin and at least one of the incompatible polymers is a polybutyleneterephthalate or a polyamide.

12. A compound according to claim 2, in which n equals zero.

13. A compound according to claim 3, in which n equals zero.

14. A compound according to claim 4, in which n equals zero.

15. A compound according to claim 1, wherein X is a hydrocarbon group.

16. A compound according to claim 15, in which n is an integer from 1 to 4.

17. A compound according to claim 2, wherein X is a hydrocarbon group.

18. A compound according to claim 17, in which n is an integer from 1 to 4.

19. A compound according to claim 3, wherein X is a hydrocarbon group.

20. A compound according to claim 19, in which n is an integer from 1 to 4.

21. A compound according to claim 4, wherein x is a hydrocarbon group.

22. A compound according to claim 21, in which n is an integer from 1 to 4.

* * * * *